United States Patent
Rudin et al.

(10) Patent No.: US 7,387,785 B1
(45) Date of Patent: Jun. 17, 2008

(54) PREPARATION FOR TREATING DISEASES OF BONE TISSUES

(75) Inventors: Vsevolod Nikolatvich Rudin, Moscow (RU); Vladimir Fedorovich Komarov, Moscow (RU); Igor Vitallevich Melikhov, Moscow (RU); Vladimir Vasillievich Minaev, Moscow (RU); Andrei Yurievich Orlov, Moscow (RU); Viktor Eygenievich Bozhevolnov, Moscow (RU); Aleksander Sergievich Pankratov, Moskau (RU)

(73) Assignee: Zakrytogo Aktsionernoe Obschestvo "Ostim", Moskau (RU)

( * ) Notice: Subject to any disclaimer, the term of this patent is extended or adjusted under 35 U.S.C. 154(b) by 247 days.

(21) Appl. No.: 10/380,746

(22) PCT Filed: Sep. 12, 2000

(86) PCT No.: PCT/IB00/01291

§ 371 (c)(1),
(2), (4) Date: Oct. 6, 2003

(87) PCT Pub. No.: WO02/22117

PCT Pub. Date: Mar. 21, 2002

(51) Int. Cl.
*A61F 2/00* (2006.01)
*A61F 13/00* (2006.01)
*A61J 33/42* (2006.01)

(52) U.S. Cl. .................. 424/426; 424/422; 424/602

(58) Field of Classification Search ............ 424/422, 424/602, 423, 426, 489, 490, 41, 44, 492; 623/16.11

See application file for complete search history.

(56) References Cited

U.S. PATENT DOCUMENTS

| | | | | |
|---|---|---|---|---|
| 4,603,050 A | * | 7/1986 | Veerme et al. | 424/602 |
| 4,668,295 A | * | 5/1987 | Bajpai | 106/690 |
| 4,871,384 A | * | 10/1989 | Kasuga | 65/30.1 |
| 5,053,212 A | * | 10/1991 | Constantz et al. | 423/305 |
| 5,573,771 A | * | 11/1996 | Geistlich et al. | 424/422 |
| 6,027,742 A | * | 2/2000 | Lee et al. | 424/422 |
| 6,136,369 A | * | 10/2000 | Leitao et al. | 427/2.27 |
| 6,201,039 B1 | * | 3/2001 | Brown et al. | 523/115 |
| 6,287,341 B1 | * | 9/2001 | Lee et al. | 623/16.11 |
| 6,344,061 B1 | * | 2/2002 | Leitao et al. | 623/23.5 |
| 6,767,955 B2 | * | 7/2004 | Jia | 524/556 |
| 2003/0113686 A1 | * | 6/2003 | Jia et al. | 433/81 |
| 2003/0180344 A1 | * | 9/2003 | Wise et al. | 424/423 |

FOREIGN PATENT DOCUMENTS

| | | | |
|---|---|---|---|
| EP | 0 786 245 A1 | * | 7/1997 |
| WO | WO 95/32707 | * | 12/1995 |
| WO | WO 99/20237 | * | 4/1999 |

* cited by examiner

*Primary Examiner*—Sharon E. Kennedy

(57) ABSTRACT

The present invention refers to an considerably improved medicinal preparation and its synthesizing method, in particular for allowing to affect the osteoreparative process due to stimulation of the prolific and functional activity of osteoblasts without risk of development of the immunologic conflict reactions. According to the invention it is provided a medicinal combined preparation for treating diseases of bone tissue containing at least a medicinal component, especially having anti-inflammatory and/or anti-bacterial properties and nano-sized crystalline hydroxyapatite having average dimensions with a length equal to 0.06 μm±50%, a width equal to 0.015 μm±50% and a thickness equal to a single transmission of crystalline lattice of the hydroxyapatite, in particular to 0.00068 μm or 0.000814 μm depending on direction of the symmetry axis of the crystalline cell.

7 Claims, No Drawings

PREPARATION FOR TREATING DISEASES OF BONE TISSUES

The invention relates to the medicine in general and in particular to a medical combined preparation for treating diseases of bone tissues.

In particular with regard to the areas of reconstruction or restoration surgery, surgical stomatology, orthopedy and/or traumatology, many operational interventions carried out on sustaining tissues of human being (bones and articulations) are made whether in conditions of a primary infected pathological nidus or a developed inflammatory process. This often happens in particular during surgical manipulation in the area of the facial bones. At the same time the prescription of an antibacterial preparation with regard to the system action is often proved to be insufficient due to a local disturbance of blood circulation in the vascular system of microcircular bed which develops in the area of the supposed surgical intervention due to the chronic inflammation or lesion. This causes some authors to show doubts in the principal expediency when a prophylactic treatment of the antibiotic therapy during operations on the bone tissue is prescribed because the medicinal effect frequently comes too late and only slightly pronounced. However, increasing the dosing of antibiotics and the duration of their application relates with an increase of the side reaction frequency.

In relation with this, a relative perspective trend for carrying out scientific researches is the creation of a medicinal compositions which being implanted in the area of pathological nidus will ensure a prolonged delivery of an antibacterial preparation in a quantity sufficient for causing an antimicrobial action. With the given purpose in clinical practice the application of polymethylmetacrylat with gentamycin adsorbed on it is described by Marish F. and Novak I. ("International Journal of plastic surgery", Prague, Avicenum, 1981, v. 23, n. 4, pgs. 233 to 237).

However, the medicinal effect may be substantially increased by imparting to a similar preparation the stimulating properties for the bone tissue growth at the site of its implantation. Using the allotransplants for this purpose is not widespread since they are not resistive to infection, persisting antigen activity, complexity of the centralised fabrication, storage and transportation. Further, osteoplastic potential of allogenic bones subsequent to some types of conservation is only slightly manifested or completely absent.

Taking into account the aforementioned, the compositions of antibiotics with calcium phosphate ceramics are of practical interest. The fabrication of the medicinal composition of antibiotics (gentamycin) with tricalcium phosphate is described by Alex R. ("Dtsch Zahnarztl Z.", 1988, Bd. 43, n. 7, s. 33-36).

However, according to this given preparation the tricalcium phosphate serves only as calcium and phosphate ion supplier and does not possess a prolific activity in respect to osteoblasts.

Furthermore, from document EP-0 664 133 a preparation is known as well for stimulating the bone tissue growth which is used as aqueous paste of highly disperse hydroxyapatite. The particles of that hydroxyapatite are nanodispersed with mean dimensions from 0.015 µm to 0.06 µm and specific surfaces of 100 m$^2$/g. In general, this synthetic nanophase hydroxyapatite is capable to stimulate the prolific activity of osteoblasts and to activate processes of reparative osteogenesis at the site of its injection. However, a disadvantage of that given preparation is the absence of an antibacterial effect in the conditions of its use in pathogenic nidus or developed inflammatory process. Moreover, due to the aforementioned particle size and relative small specific surface the particles are capable to form aggregates having reduced biological activity and sorption capacity.

Virtually, the most similar preparation to the proposed one involves a medicinal film for treating parodontosis (PCT/RU95/00111). The film contains a medicinal preparation and a polymeric support. The highly disperse hydroxyapatite with concentration of 10% to 40% applied to weight is used as medicinal component. Additionally, the medicinal film also contains antibacterial components and/or antioxidants with the following ratio of components (% applied to weight): antibacterial substances 10% to 40%; antioxidants 0 to 0.5%; the rest is a polymeric support.

However, one of the main disadvantages of that given preparation concerns its application domain which is limited in substantial to a treatment of parodontosis and concomitant diseases and consequently its impossibility to use the preparation for treating bone defects in traumatology and especially in closed traumas (by means of injections) in particular because of lacking plasticity and fluidity of the preparation. In addition the known preparation causes a lack of prolonged action and a limited time of medicinal action. Furthermore, the low content of anti-inflammatory additions in the preparation does not allow to successfully use the preparation in treating purgatory bone wounds. Moreover, the fact that the film itself should be dried up to a residual humidity of 5% to 7% results in passivity of hydroxyapatite and reduces its capability to stimulate prolific activity of osteoblasts, that in turn decreases activity of hydroxyapatite in reparative osteogenesis at the site of the preparation injection. Finally, the composition itself is lacking rather high biological activity because of the consisting of hydroxyapatite with particle size from 0.015 µm to 0.06 µm.

A main object of the present invention is to provide an considerably improved medicinal composition allowing to affect the osteoreparative process due to stimulation of the prolific and functional activity of osteoblasts without risk of development of the immunologic conflict reactions.

Advantageous and/or preferred embodiments are subject of the respective depending claims.

According to the invention the above-mentioned object is solved by synthesising medicinal preparations containing at least a medicinal component especially having anti-inflammatory and/or anti-bacterial properties and nano-sized crystalline hydroxyapatite according to the International Application PCT/EP00/06194 the disclosure of which is herein completely incorporated by means of reference. A such medicinal preparation containing that nano-sized crystalline hydroxyapatite has an increased medicinal effect of stimulation of reparative osteogenesis and high biological activity. The size and shape of the particles having a length l being in the order of 0.06 µm±50%, a width d being in the order of 0.015 µm±50% and a thickness h being equal to the size of a single transmission of a crystal lattice of the hydroxyapatite and thus equal to h=0.00068 µm or h=0.000814 µm depending on the direction of the symmetry axis of the crystalline cell are maximally adapted to the bone tissue growth. According preferred embodiments of the invention, the specific surface of the nano-sized hydroxyapatite is of 900±50 m$^2$/g and the concentration of the nano-sized crystalline hydroxyapatite may varying from 5% to 100% of the preparation.

In order to provide a preparation that may be directly implanted, for example by injections, into a nidus area of in substantially any bone tissue the inventive medicinal combined preparation according to a further embodiment is produced as being a paste providing sufficient plasticity and/or fluidity. Purposely a such paste is produced as being homogeneous, in particular since the presence of any local inhomogeneous zone within the paste may result in creating plugs preventing its use in closed traumas.

In a further preferred inventive embodiment for ensuring a prolonged delivery of the antibacterial preparation in a required dosage, especially when synthesising the medicinal preparation as a paste for an internal injection into bone the inventive preparation additionally comprises biopolymers. A such addition results in the prolonged delivery of antibacterial components from the implantation site to surrounding bone tissue in dosage substantially exceeding its inhibiting concentration with respect to the principal types of pathogens. Basing on clinical experiments in substantial any bioresolving polymer biocompatible with organism may be chosen as a biopolymer, for example polyvinylpyrrolidon, oxyisopropylcellulose, and proteins as well.

For carrying out a directed antimicrobial action at the site of a pathologic nidus with a simultaneous reduction of total toxic action on an organism including a decreased rate of the side effects the medicinal combined preparation advantageously may containing anti-infective (bacterial) agents in a concentration of 0 to 50%, anti-inflammatory agents in a concentration of 0 to 50%, proteins in a concentration of 0 to 30% and/or antioxidants in a concentration of 0 to 20%. Depending on the specific application it has been turn out that the composition of the inventive preparation practically may involve anti-inflammatory and antibacterial components, especially from the groups of a natural and semisynthetic penicillin, cephalosporins, macrolides, aminoglycosides, group of levomycetins, lincosamines, flouroquinolons, polymixines, teracyclines, carbapenems, rifampicines, triazoles, derivatives of nitroimidazol, sulphanylamides, quinolons, derivatives of 8-oxyquinoline, nitrofuran, quinoxolin, and as well antioxidants, as for example superoxide dismutase, catalase, peroxydase, emixypin and other. Also introduced proteins may play a medicinal role, as for example it is known that protease C may accelerate the resolution of exudate.

In substantial, the inventive preparation can be manufactured by two ways. The first one involves the dissolving of the required medicinal substances and, as necessary of the biopolymer in the aqueous part of a hydroxyapatite solution with keeping the mixture during that time capable to dissolve the additional components. A second way of manufacturing involves the dissolving of the medicinal substances in a solution of biopolymer with subsequent mixing of the produced mixture with nano-sized crystalline hydroxyapatite.

Subsequent to a procedure of mixing the resulting mixture can be additionally homogenised. The component ratio may be chosen in dependence on the medicinal prescription.

Medicinal preparations according to the invention, especially manufactured as a homogeneous paste may then be advantageously prescribed for in substantially any clinical treatment of various inflammatory and/or destructive diseases of bone tissue.

Basing on experimental clinical studies of activity of varied inventive medicinal preparations comprising the nano-sized crystalline hydroxyapatite according to the disclosure of the International Application PCT/EP00/06194 with antibacterial properties the invention is described in more detail and in view of preferred embodiments The results of the conducted clinical studies have shown that implantation of the composition comprising nano-sized crystalline hydroxyapatite with antibiotics is not accompanied by marked prolongation of the operative intervention compared with the patients of a control group, or complicating its technique. The produced form as homogeneous plastic paste is convenient for its application for allowing to fill uniformly cavities of the bone defects. A procedure of the implantation of the preparations is not accompanied by discomfort or painful feelings. Substantially, in no one case hypersensitive reactions develops.

The most efficiency of the medicinal compositions was shown in the treatment of patients with suppuration of the bone wound and local post-traumatic osteomyelitis. Thus, the implantation of the given preparations into the lesion zone with combination of the inner rigid fixation of the bone fragments has permitted to radically reduce the average number of days of disablement for patients with inflammatory complications of mandible fractures from 60 days to 17.7 days with a qualitative higher living standard, and to save patients of these groups from using cumbrous and rather inconvenient extramouth devices. Relapses of the inflammatory processes have not been observed.

When treating the patients with cyst neoplasm complicated by inflammatory processes, the implantation of the medicinal compositions based on nano-sized crystalline hydroxyapatite favours to break inflammatory processes compared with the control group (exudation from the wound, for example, was revealed for 23.8% of the patients in the main group and for 64.4% in the control group), and also an earlier restoration of the bone structure in the defect zone.

Applications of the compositions of the nano-sized crystalline hydroxyapatite with antibacterial and other active preparations in the complex treatment of patients with parodontal diseases have shown their efficiency which is manifested by positive dynamics of the parodontal indexes. During treatment, for example, the so-called PMA index values change from 68.4+4.9 to 6.7+3.4, and the depth of the parodontal pockets decreases from 5.54 mm±0.28 mm to 2.17 mm±0.19 mm. The preparations under studies by a number of clinical factors do not yield to tissue transplants but in some cases exceed them, being at the same time free from some of their disadvantages, in particular concerning immunothropy, complexity of centralised production, storage and/or transportation.

Thus the medicinal compositions of the nano-sized crystalline hydroxyapatite with antibacterial and other preparations are very efficient medicinal means to treat patients with various inflammatory destructive diseases of the bone tissue.

Subsequently, some examples of clinical observations with regard to different applications of inventive medical combined preparations are described.

1. A preparation comprising a composition of 33% lincomycine hydrochloride 33% nano-sized crystalline hydroxyapatite, 7% polyvinylpyrrolidon, 2.7% water.

The toxicity studies of the given composition have been carried out on male rats with hypodermic, intraperitoneal or peroral injection. Injection of the preparation into animal stomach does not result in their death and intoxication symptoms have not been observed. The value DL 50 ("dosis letalis") exceeds 18000 mg/kg for hypodermic injection (maximal possible dose of injection). In a case of intraperitoneal injection, the value DL 50 is equal to 8500 mg/kg. Sensitising properties of the preparation have not been observed (studies are carried out on guinea-pigs).

During subacute experiments the mortality of animals has not been observed. No deviations in the functional indexes of the nerve system, liver, kidneys, composition of the peripheral blood, mass coefficients of visceral organs have been registered, and their macrostructure does not change in comparison with the control group.

In one month after injection of composition its mutagen effect on the rat marrow has not been disclosed.

Thus, the conducted toxicity expertise has disclosed no additional restrictions (compared with those which have already established for lincomycin) for wide medical application of the composition under study. At the same time during a study of influence of the preparation on the functional and prolific activity of osteoblasts in vitro it was shown that its cytotoxic action is 10 times less than of lincomycin. At the same time antibacterial activity of the antibiotic does not decrease as was proved by method of serial breeding in vitro.

Pharmacokinetics of lincomycin has been studied by partition of the tritium labelled preparation in the visceral organs and tissues of rats after injection of the medicinal compositions into standard defect of mandible.

It was found that at the site of composition implantation, the concentration of lincomycin is kept ten-hundred times exceeding a minimal inhibiting concentration with respect to principal micro-organisms sensitive to lincomycin during no less than 7 days. At the same time the concentration of antibiotics in the visceral organs and tissues was minimal. Data of microbiological studies witness an active diffusion of lincomycin from the preparation injection area into the surrounding bone.

All cases using the nano-sized crystalline hydroxyapatite with antibiotics result in proved decrease of appearance extent of the inflammatory reaction and stimulation of reparative osteogenesis. Contrary to a case when after 14 days of lesion the control group reveals mainly micro-abscesses and polymorpho-cellular infiltration, using the composition of hydroxyapatite with antibiotics a local oedema is observed and the cavity of wound canal is filed with active fibroblasts for the same time of observation.

In clinics the medicinal composition of the nano-sized crystalline hydroxyapatite with antibacterial substances has been tested in treatment of 392 persons among which there were patients with facial bone fraction and long tubular bone extremities, post-traumatic osteomyelitis, cyst neoplasm of jaw, parodontitis. The preparation was injected during the operation intervention after removal of the necrotic bone, pathologically modified tissue, thorough washing of the bone cavity with antiseptic solutions. If necessary the stable fixation of the bone fragments was preliminary undertaken. The observation conducted on basis of the clinical, laboratory and radiographic data.

a) Patient X.: Radicular cyst in zone 4. A filling material in excess is placed into a cyst-cavity. Operation of cystectomy with resection of superior radix 4 and removal of the filling excess has been performed. During the operation the inventive preparation comprising nano-sized crystalline hydroxyapatite and lincomycin has been injected into the formed bone cavity. According to a control radiograms registered after 2 months and 12 days the post operational defect was completely filled with bone regenerated.

b) Patient A.: On the primary radiograms a cyst cavity of mean size with a protruded radix 5 was observed. Into the formed bone cavity the medical preparation comprising nano-sized crystalline hydroxyapatite composition and lincomycin has been introduced. According to the radiogram registered after 3 months subsequent to the operation the bone defect was completely filled with the shadow of newly formed bone.

2. A preparation comprising a composition of 4.75% metronidazol, 28.5% nano-sized crystalline hydroxyapatite, 66.75% distilled water.

Toxic activity studies of this composition of the inventive medical preparation have been conducted on two type of test animals, namely on rats and rabbits.

Its introduction with maximal possible doses (i.e. with hypodermic, peritoneal and peroral injections of 18 g/kg, 10 g/kg and 12 g/kg of the animal weight, respectively) has not induced a reduction of mobility or weakness or an increasing of the breathing rate of the test animals. A mortality of the tested animals has not been observed during complete experiment period. This enables to classify the given composition to low toxic substances. Further, the composition does not locally irritate the eye mucous membrane and skin surface during one and repeated applications.

Data of chronic experiment have shown that the preparation unfavourably may affect the test animal organisms if applied as a hypodermic dose of 7.28 g/kg. It manifests in loss of body weight, change of functional indexes of nervous system, small leukocytosis within two weeks, increasing the so-called AcAT activity in one month and two weeks and increasing the urea in blood within one month of the experiment. If the composition is injected as a hypodermic dose of 3.62 g/kg and of 3.0 g/kg intraperitoneally, the functional indexes of the tested animals did not practically change in comparison with the control animals.

Post-mortem examination of the tested animals when the chronic experiment is finished has not revealed inflammatory phenomena, haemorrhage or blood overflow in the visceral organs.

Taking into account that in the clinical practice using injection of the preparation with the indicated doses is not supposed it may be stated that the conducted toxicological expertise does not reveal contradictions for the given composition to be used in the medical practice.

The preparation incubation with multi-layered cultures of osteoblasts in vitro has shown the absence of cytotoxic action.

The Introduction of the composition into a bone defect ensures the prolonged delivery of metronidazol at the pathologic nidus area into surrounding bone tissue. During 6 days of the experiment a bone fragment taken in the vicinity of the implantation suppresses the culture growth of *Bacteroides fragilis* within a diameter of about 7 to 3 mm. The presence of metronidazol in blood serum of the test animals has been observed within 8 days after a single injection of the given preparation.

Implantation under study of the medicinal composition into a standard bone defect during a developing of suppurative inflammatory process induced by an infection of an associated microbial culture of *Bacteroides fragilis* and *Staphylococcus aureus* within 7 days results in a decrease in content of anaerobes by more than 150 times.

Histology study has shown that in 7 days after an introduction of the given preparation the tested animals reveal substantially lower manifested inflammatory reaction and the cavity of wounded canal is filled with fibroblast tissue. Regarding the group of control animals for the same period observation, at the same time a large number of micro-abscesses and multiple haemorrhages are registered and the reparative processes are not pronounced. In 56 days of the experiment (after 49 days as the composition was implanted) a nidus of fascicle bone and formation of osteogen structures were noted in the area of wounded defect.

Clinical studies are carried out over 93 patients with post-traumatic inflammatory complications of the facial bone fractures and long tubular extremity bones, suppurative jaw cysts, parodontitis. The implantation of the medicinal composition was conducted according to the aforementioned scheme.

a) Patient C.: Diagnosis of a generalised parodontitis of mandible. Osteogingivoplastics has been performed with implantation of the above mentioned inventive preparation comprising nano-sized crystalline hydroxyapatite and metronidazol into the parodontal pockets. Further the rational denture has been done. The control radiogram taken in 8 months shows complete restoration of the bone tissue in the area of the existed pockets.

b) Patient P. (22 years old), while driving a car has been injured in an accident. An open screw-type fracture of the diaphysis of the tibia (at left side) is diagnosed. Skeletal traction is used for its treating. Subsequent to the treating a traumatic osteomyelitis has developed. According to a Roentgenogram taken in six months after trauma, bone sequesters and symptoms of false joints are determined in the fracture line. Data on bone consolidation are not available.

An operation with fistula carving, removal of pathologically deformed tissue in a fracture fissure has been carried out and a composition comprising nano-sized crystalline hydroxyapatite and metronidazol was injected into formed bone defect with subsequent fixation of the bone parts with a surface plate: The post operation period proceeded smoothly and inflammatory signs are cut. Within 3 months after the operation a mature bone callosity has been formed and the fracture line is not revealed.

3. A preparation comprising a composition of 0.5% superoxide dismutase, 15% lincomycin, 17% gentamycin, 30% of nano-sized crystalline hydroxyapatite, polyvinylpyrrolidon and 27.5% of water.

a) Patient P.: Post-trauma osteomyelitis of a mandible. Abscess at the undermandible site. Upon entering the clinics the phlegmon is cut. After cutting the acute inflammatory phenomena, an operation of sequestectomy is carried out and, thereafter, the large bone defect is formed along the lower edge of the mandible. The aforementioned preparation has been injected into the formed cavity. Bone fragments are fixed by an on-bone mesh plate. Despite that an internal fixing piece was directly installed in the area of inflammatory site of the bone tissue, the post-operational period proceeded smoothly. A control X-ray taken within six months at the area of the previous defect reveals newly formed bone tissue whose density is not different from the origin (mother) bone. The plate is removed and in the range of the previous defect the mature bone is discovered.

b) Patient C.: Large keratocyst is found on branch, angle and body of the mandible. A cystectomy accompanied by the removal of 7.8 teeth protruding into the cyst cavity is performed. During the operation the preparation is injected into the formed cavity. A control X-ray taken within 8 months shows that the defect is completely filled with a newly formed mature bone tissue whose density is not different from the density of the origin bone.

4. A preparation comprising a composition of 3% metronidazol, 35% nano-sized crystalline hydroxyapatite, 7% albumin and 55% water.

a) Patient C., 45 years old, after car accident (Oct. 16, 1998) entered with open splintered fracture of the middle third of the right femur with a shift and the wound was contaminated with cloth pieces, sand and so on. He was operated on Nov. 16, 1998 by a primary surgical treatment of the wound, osteosynthesis of the right femur with a plate accompanied with an injection of 10 grams of the aforementioned preparation into the fragments. The wound is healed by the primary tension (no symptoms of inflammatory reaction were observed), the patient left hospital for ambulatory observation. The patient did not follow recommendations—complete load on the wounded leg right away after discharge from hospital. In 4 weeks after operation the X-ray shows the formation of the bone callosity. In 12 weeks the X-ray shows strengthening of the bone callosity and its calcification. In 20 weeks the knitting of the fragments is observed clinically and by X-ray. The patient has not been observed from 21 to 32 weeks. After 52 weeks the patient took another observation where the complete knitting of the fragments is proved by X-ray (The fracture of a screw). The fixation unit is removed. The Function of injured extremity proved to be completely restored.

Despite great contamination of the wound and violation of the recommendations by the patient resulting in the secondary displacement of the fragments, functioning of the injured extremity is completely restored.

b) Patient B., 39 years old, (Mar. 30, 1999) with an open fracture of both bones of left forearm with displacement has entered a hospital after 6 weeks with a purulent discharge from the wound. The fragments of the forearm bones were observed in the wound. Surgical treatment of the wound and osteosynthesis of the bones of the left forearm (radius by a plate and ulna by a peg) are carried out together with introduction of the aforementioned preparation of 10 g (5 g into each bone) amid the fragments. The wound is healed by primary tension and no inflammatory phenomena are observed). After trauma the knitting of the bones is observed clinically and is proved by X-ray in 11 months, the fixating unit is removed.

Despite the purulent wound no inflammatory phenomena are discovered after the operative treatment, the wound is healed with the primary tension, complete knitting of the bones started more early and no complications are observed.

c) Patient P., 18 years old, after car accident got open fragmented fracture of diaphysis of the left femur with a displacement. On entering a hospital the wound is surgically treated and skeletal traction is carried out. In 10 weeks after surgical treatment of the wound the efflux of pus from the wound appeared. Secondary surgical treatment and osteosynthesis of the left femur are performed together with introduction of the aforementioned preparation into the fragments. The wound is healed with primary tension. No inflammatory reactions in soft and bone tissues are discovered. In 11 months the femur knitting is proved clinically and by X-ray. Fixating unit is removed. Despite purulent inflammation, the left femur knitting took place more early and no complications are observed.

d) Patient B., 60 years old, having trauma after car accident as open transtrochanter fracture of the right femur with displacement entered with the large contamination of the wound where cloth pieces, asphalt and sand amid the fragments are observed. Surgical treatment of the wound and osteogenesis of the upper third of the right femur by the wedge plate are performed together with introduction of the aforementioned preparation into the area of the fragments. The wound is healed by a primary tension and no inflammation is revealed. After 7 months the complete knitting of the femur is revealed and functioning of the low extremity is restored.

Despite initially infected bone wound, the consolidation process has proceeded without complications.

e) Patient P., 63 years old, with closed transcervical fracture of the right femur cervix with background of osteomyelitis of bones of the right shin. Percutaneous osteosynthesis of the right femur cervix by three canalised screws is performed together with introducing 30 g of the aforementioned preparation into the fragments through the canals of the screws. Puncture openings are healed by a primary tension. The fracture is proved clinically and by X-ray to be knitted in 6 months without complications.

Despite osteomyelitis of the patient, the complications did not appear and the fracture is knitted.

Thus, the medicinal compositions especially of the above preparations are very efficient medicinal means to treat patients with various inflammatory destructive diseases of the bone tissue. For synthesising such inventive preparations the medicinal substances can be dissolved in a solution of biopolymer with subsequent mixing of the produced mixture especially with a paste of nano-sized crystalline hydroxyapatite with homogenisation of the mixture or can be dissolved, if necessary together with a biopolymer, in the aqueous part of a hydroxyapatite solution with keeping the mixture during that time sufficient to dissolve the additional components with subsequent homogenisation of the mixture. The ratio of the components, however, may be chosen in dependence on the medicinal prescription.

The invention claimed is:

1. Medicinal combined preparation for treating diseases of bone tissue containing at least a medicinal component, and nano-sized crystalline hydroxyapatite having average dimensions with a length equal to 0.06 μm±50%, a width equal to 0.015 μm±50% and a thickness equal to 0.00068 μm or 0.000814 μm depending on direction of the symmetry axis of the crystalline cell and wherein the specific surface of nano-sized crystalline hydroxyapatite is of 900+50 $m^2$/g.

2. Medicinal combined preparation according to claim 1, wherein said preparation contains biopolymers, especially for regulating the duration of delivery of anti-inflammatory and/or antibacterial medicinal substances to a pathologic nidus zone.

3. Medicinal combined preparation according to claim 1, wherein the medicinal component has anti-inflammatory and/or anti-bacterial properties.

4. Medicinal combined preparation according to claim 1, wherein the concentration of the nano-sized crystalline hydroxyapatite is 5 to 100% of the preparation.

5. Medicinal combined preparation according to claim 1, wherein said preparation contains anti-infective (bacterial) agents in a concentration of 0 to 50%,
anti-inflammatory agents in a concentration of 0 to 50%,
proteins in a concentration of 0 to 30%,
antioxidants in a concentration of 0 to 20%,
a polymeric basis in a concentration of 0 to 50%
and/or water in a concentration of 0-95%.

6. Medicinal combined preparation according to claim 1, wherein said preparation is produced as being a paste.

7. Medicinal combined preparation according to claim 1, wherein said preparation is produced as being homogeneous.

* * * * *